United States Patent [19]

Okita

[11] 4,234,535
[45] * Nov. 18, 1980

[54] PROCESS FOR PRODUCING POROUS POLYTETRAFLUOROETHYLENE TUBINGS

[75] Inventor: Koichi Okita, Osaka, Japan

[73] Assignee: Sumitomo Electric Industries, Ltd., Osaka, Japan

[*] Notice: The portion of the term of this patent subsequent to Apr. 4, 1995, has been disclaimed.

[21] Appl. No.: 47,470

[22] Filed: Jun. 11, 1979

Related U.S. Application Data

[60] Continuation of Ser. No. 853,792, Nov. 21, 1977, abandoned, which is a division of Ser. No. 751,876, Dec. 17, 1976, Pat. No. 4,082,893.

[30] Foreign Application Priority Data

Apr. 29, 1976 [JP] Japan ................................ 51/49671
Dec. 17, 1977 [JP] Japan ............................... 52/155226

[51] Int. Cl.³ ............................................. B29C 17/07
[52] U.S. Cl. ................................. 264/519; 264/127; 264/288.8; 264/568
[58] Field of Search ............. 264/127, 519, 568, 288.8

[56] References Cited

U.S. PATENT DOCUMENTS

| | | |
|---|---|---|
| 3,050,786 | 8/1962 | St. John et al. . |
| 3,417,176 | 12/1968 | Anderson et al. . |
| 3,953,566 | 4/1976 | Gore ................................... 264/175 |

FOREIGN PATENT DOCUMENTS 836024 7/1960 United Kingdom ..................... 264/127

*Primary Examiner*—James B. Lowe
*Attorney, Agent, or Firm*—Sughrue, Rothwell, Mion, Zinn and Macpeak

[57] ABSTRACT

A porous polytetrafluoroethylene tubing, useful as artificial internal organs or industrial filtering materials for, for example reverse osmosis, ultrafilteration, etc., having a microporous fibrous structure in which the fibrous structure is composed of fibers and nodes connected with each other and the microporous fibrous structure differs between the outer surface portions of the tubing and the inner surface portions of the tubing, and a process for producing the porous resin tubing comprising heating a tubing made of an unsintered polytetrafluoroethylene under conditions in which the tube is stretched at least in the longitudinal direction of the tubing and such that the outer surface of the tubing is heated above about 327° C. and the inner surface of the tubing is heated to a temperature below the temperature of the outer surface.

11 Claims, 8 Drawing Figures

PROCESS FOR PRODUCING POROUS POLYTETRAFLUOROETHYLENE TUBINGS

This application is a continuation application of Ser. No. 853,792, filed Nov. 21, 1977, now abandoned in turn a Divisional Application of Ser. No. 751,876, filed Dec. 17, 1976, now U.S. Pat. No. 4,082,893.

BACKGROUND OF THE INVENTION

1. Field of the Invention

The present invention relates to a porous polytetrafluoroethylene tubing and, more particularly, it relates to a porous polytetrafluoroethylene tubing having a composite fibrous structure in which the outer surface portion differs from the inner surface portion in structure. Moreover, the invention also relates to a process of producing such a polytetrafluoroethylene tubing.

2. Description of the Prior Art

Porous polytetrafluoroethylene tubings are known to be produced by processes as described in, for example, Japanese Patent Publication No. 13560/67 and U.S. Pat. No. 3,953,566. The features of these processes are as follows: That is, an unsintered polytetrafluoroethylene mixture containing a liquid lubricant is shaped into a sheet, rod, or tube by extrusion, rolling, or a combination of these techniques and the shaped material thus formed is stretched in at least one direction in the unsintered state, heated to a temperature higher than about 327° C. in a stretched state.

The structures of the porous products obtained with these known processes may differ to some extent according to the stretching ratio, the temperature at stretching, the stretching speed, etc., employed, but the porous products obtained have a micro-composite structure composed of nodes connected together by small fibers and the spaces surrounded by the nodes and the fibers form the fine cavities of the porous structure. In general, by increasing the stretching ratio in these known processes, it is possible to increase the length of the fibers, decrease the size of the nodes, and increase the porosity of the porous structure.

That is, it is generally known that porous fibrous articles having a comparatively simple fibrous structure such as porous sheets, porous rods, porous tubes, etc., can be produced.

SUMMARY OF THE INVENTION

An object of this invention is to provide a porous polytetrafluoroethylene tubing having a specific composite structure apropriate for particular purposes, practically speaking, such tubular fibrous article substitutes as artificial blood vessels, artificial tracheas, artificial esophagi, artificial biliary ducts, etc.

A particular object of this invention is to provide a porous polytetrafluoroethylene tubing suitably used as a specific tubular articles of which the outer surface differs from the inner surface in fibrous structure.

Another specific object of this invention is to provide a porous polytetrafluoroethylene tubing suitably used as an industrial filter tubing for gases or liquids capable of preventing blocking and a reduction in filtering resistance when gases or liquids permeate through the porous wall of the fibrous tubing.

Still another specific object of this invention is to provide a porous polytetrafluoroethylene tubing suitably used as a gasket or packing for sealing.

Another object of this invention is to provide a process for producing the above-described porous polytetrafluoroethylene tubings in an industrially and economically profitably manner.

The above objects of this invention are attained by the present invention as set forth below in detail.

Accordingly this invention provides a porous polytetrafluoroethylene tubing of which the outer surface portion differs from the inner surface portion in fibrous structure including the size, length, and direction of fibers and the form of nodes connected to the fibers of the tubular article.

Also, according to another embodiment of this invention, this invention provides a process of producing a porous polytetrafluoroethylene resin tubing having a composite structure in which the outer surface portion differs from the inner surface portion in fibrous structure of the tubular porous article by forming a tube of an unsintered polytetrafluoroethylene mixture containing a liquid lubricant, stretching the tube at least one direction and heating the tube in stretched state in such a manner that the temperature of the outer surface of the tube is higher than about 327° C. and the temperature of the inner surface of the tube is lower than that of the outer surface thereof.

DETAILED DESCRIPTION OF THE INVENTION

Artificial organs made of plastics must have the following characteristics; (1) they must not be denatured by the fluids in the living body, (2) they must be chemically inert, (3) they must be non-inflammatory and must not cause a foreign body reaction, (4) they must not be carcinogenic, and (6) their mechanical properties such as tensile strength, etc., must not change with the passage of time. Polytetrafluoroethylene meets all of these requirements and is one of the most useful plastics for the purpose. However, since considerable difficulty is usually encountered in the shaping or working operations of the resin, the excellent characteristics of the resin as indicated above have not yet been fully utilized.

In the field of industrial filtering techniques, reverse osmosis, ultrafiltration membranes, etc., have now been developed for many purposes. These membranes have a composite structure of which the very thin outer surface layer for performing the filtering function has a fine microporous structure but the inside support layer for maintaining the mechanical strength of the membrane has a comparatively large microporous structure and known examples of these membranes include not only planar or sheet like membranes but also tubular articles. However, these conventional membranes are made of celluloses or polyamides and membranes made of a polytetrafluoroethylene having a composite structure are not yet known. Furthermore, when such a porous tubular article is used as a tubular gasket the tubular article must have a structure in which the outer surface of the tubular article is hard and the inside surface thereof is soft and compressible.

According to the process of this invention, a fine powder of an unsintered polytetrafluoroethylene is uniformly mixed with a liquid lubricant and after pre-forming the mixture by compression, the mixture is shaped into a tube by means of, for example, a ram extruding machine. Then, after removing the liquid lubricant from the tube thus formed by evaporation or extraction, the tube is stretched in at least one direction, ordinarily in the longitudinal direction of the tube. These procedures as indicated above are the same as or are similar to those employed in known processes as described before but the subsequent step where the tube thus stretched is heated to a temperature higher than about 327° C. for sintering is the step that has never been employed in these known processes and is a most important step in this invention.

In heating the tube thus stretched, it is possible to supply heat from the inside of the tube only but the tube is usually and advantageously heated from the outside. In this case, by heating the tube while passing air through the inner cavity of the tube for cooling, it becomes possible to change the porous fibrous structure of the outer surface of the tubing from the porous fibrous structure of the inner surface of the tubing.

The porous fibrous structure has a microporous fibrous structure comprising small fibers and nodes connected together by the small fibers.

In the first embodiment of the porous polytetrafluoroethylene tubing of this invention, the porous resin tubing has a specific microporous structure in which, for example, the diameter of the fibers is smaller at the inner surface of the tubing but the diameter of the fibers at the outer surface of the tubing larger than at least twice the diameter at the inner surface of the tubing, but the size of the nodes at the inner surface of the tubing is almost the same as that of the nodes at the outer surface of the tubing.

The size of the nodes and the length of the fibers depend on the stretching conditions of the tube but the diameter of the fibers does not change greatly when the tube is stretched in one direction. However, it is known that when the tube is stretched in two or more directions, the diameter of the fibers is reduced suddenly and the porous tubing of this invention in the first embodiment has the feature in terms of porous fibrous structure that the outer surface of the tubing differs from the inner surface of the tubing in the size and length of the fibers and in the form of the nodes.

Furthermore, in the second embodiment of the porous tubing of this invention, the length and the diameter of the fibers at the inner surface of the tubing are the same as those of the fibers at the outer surface but the form of the nodes is a long or slender ellipsoid at the outer surface portion of the tubing while at the inner surface of the tubing, the ellipsoidally shaped nodes is divided in the longitudinal direction thereof to shorten markedly the long axis of the ellipsoid and some of the nodes there have a form nearly spherical. The second embodiment of the porous tubing of this invention has the feature that the nodes at the inner surface portion of the tubing have the form of an ellipsoid having a short long axis and the nodes at the outer surface portion of the tubing have the form of ellipsoid having a long axis whose length is longer than twice that of the ellipsoidal nodes at the inner surface of the tubing.

In the third embodiment of the porous tubing of this invention, not only the length of fibers but also the form of the nodes differ between the inner surface of the tubing and the outer surface of the tubing. In this case, the length of the fibers is shorter at the inner surface of the tubing and the length of the fibers at the outer surface of the tubing is more than 1.5 times the length of the fibers at the inner surface and the nodes at the outer surface of the tubing have the form of an ellipsoid having a slightly shortened long axis while the nodes at the inner surface of the tubing have the form of an almost flat body and lose the form as an ellipsoid.

The fibrous structures in the three embodiments of this invention indicated above are related to each other to some extent. That is, the fibrous structure at the inner surface of the tubing in the first embodiment of this invention is the same as the fibrous structure at the outer surface of the tubing in the second embodiment of this invention. Moreover, the fibrous structure at the inner surface of the tubing in the second embodiment of this invention is the same as the fibrous structure at the outer surface of the tubing in the third embodiment of this invention.

The advantages of the fibrous structure wherein the diameter of the fibers differs between the outer surface and the inner surface of the tubing will be explained below in detail. With respect to artificial tubings, vascular prostheses, such as, for example, artificial blood vessels, artificial tracheas, esophagi, biliary ducts, etc., must have such fine pores at the inner wall that when the vascular prostheses is implanted into a living body, blood, body fluids, or bile must not leak through the inner wall of the vascular prostheses. However, during the patients healing, the outer wall of the vascular prostheses thus implanted in the patient begins to be covered by connective tissue, the connective tissue is gradually replaced by the fibrous tissue thus entering through the outer wall of the vascular prosthesis, and afterwards the fibrous tissue is strongly connected to the neo-intima which has grown at the inner wall of the vascular prosthesis. For the purpose, the artificial tubing used must have comparatively large pores at the outer wall of the vascular prosthesis.

The diameter of the pores of the vascular prosthesis necessary for making the entrance of the fibrous tissue possible is at least about 2 microns and if the diameter of the pores of the vascular prosthesis is less than about 2 microns, the fibrous tissue does not enter into the pores of the prosthesis wall. If the fibrous tissue in the pores of the wall is not connected to the neo-intima, the neo-intima cannot continue its growth at the inner surface of the vascular prosthesis. Thus, the diameter of the pores at the outer surface of the vascular prosthesis is generally larger than 5 microns and it has usually been attempted to use wovens or knittings of polyethylene, nylon, Dacron, etc., but satisfactory vascular prosthesis have not yet been obtained.

From these circumstances as indicated above, it will be understood that the composite structure of the porous tubing of this invention is quite excellent for the purpose if the tubing has pores of, for example, a 10 micron diameter at the outer surface of the tubing and pores of, for example, a 3 micron diameter at the inner surface of the tubing.

For industrial purposes, porous tubings must be capable of filtering, concentrating, or resolving different components and at the same time to have the ability for treating a large amount of materials. Filtration or resolution can be practiced better if the pore size distribution grows smaller but in order to increase the amount of materials treated in a definite period of time, the number of pores of the tubing must be increased or the thickness of the wall of the tubing must be made as thin as possible. However, it is very difficult to increase greatly the number of pores of the tubing within the specific conditions used in producing the tubing and further an excessive reduction in the thickness of the tubing is accompanied by a reduction in the mechanical strength of the tubing. Hence such a means cannot be employed from a practical standpoint. Therefore, in these industrial fields, the porous tubing of this invention is also excellent as it has the composite fibrous structure in which the diameter of the pores at the inner surface of the tubing differs from the diameter of the pores at the outer surface of the tubing.

The relationship between flexibility and tear resistance as one of the features of the porous polytetrafluoroethylene tubing of this invention is explained below.

The flexibility of a porous tubing increases as the porosity of the tubing increases but in this case, the tear resistance of the tubing decreases. The reduction in tear resistance of the porous tubing itself restricts the applicable fields of the porous tubing.

The tear resistance only of the porous tubing may be increased by reducing the porosity or by increasing the thickness of the wall of the porous tubing but the flexibility of the porous tubing is greatly reduced by employing these means.

One of the important objects of this invention is to increase the tear resistance of the porous tubing without greatly reducing the flexibility of the porous tubing and it has been found that the object of this invention can be attained by employing a different fibrous structure between the inner surface and the outer surface of the tubing.

In particular, in order to improve the tear resistance of a porous polytetrafluoroethylene tubing, it is important to align the direction of the small fibers forming the wall of the porous tubing. Since the aligned direction of the small fibers coincides with the stretched direction of the tube, the aligned direction of the small fibers coincides with the longitudinal direction of the porous tubing when the tubing is stretched in the longitudinal direction only.

When the porous tube is expanded in the radial direction only, the arranged direction of the small fibers is also in the radial direction of the porous tubing. Therefore, the tear resistance of the porous tubing can be increased by expanding the porous tube in the radial direction as far as possible. However, when a mixture of a fine powder of a polytetrafluoroethylene with a liquid lubricant is shaped into a tube using an extruding machine, the polytetrafluoroethylene is arranged in a fibrous state in the extruded direction of the tube by the shearing force which occurs at the contact face with the metallic mold.

The fibrous arrangement proceeds sufficiently in the longitudinal direction of the tube and gives a considerable strength in the longitudinal direction, but in this case fibrous arrangement scarcely occurs in the radial direction of the tube and hence the strength in the radial direction of the tube is only about ⅓ to 1/5 of the strength in the longitudinal direction of the tube. Therefore, a porous tubing may be obtained by expanding the radial direction only of the tube but the yield of the porous tubing thus obtained must be considerably lowered since many crackings occur.

In this invention, a tube is first stretched in the longitudinal direction at a definite ratio to form small fibers aligned in the longitudinal direction of the tube and then the tube is expanded in the radial direction of the tube to form small fibers aligned in the radial direction of the tube, whereby a porous tubing is obtained with excellent flexibility and tear strength. As a matter of course, a porous tubing having the same structure and properties as above can be obtained by first performing the expansion in the radial direction of the tube and then stretching the tube in the longitudinal direction. However, when the longitudinal stretching is carried out first, porous tubings can be obtained in stable quality.

The expansion of the tube in the radial direction can be performed continuously creating a vacuum around of the tube.

The number, length, and size of the small fibers formed in the longitudinal direction and the radial direction of the tubing by the stretching in the longitudinal direction and the expansion in the radial direction change as a matter of course depending on the extent of the stretching and expansion and they can be suitably selected depending on the desired values of porosity, pore diameter, flexibility, and tear resistance. When the stretching ratio is substantially the same as the expansion ratio of the tube, the directions of the small fibers are uniformly distributed radially centering around spherical nodes. In this case, the direction of the fibers differs between the inner surface and the outer surface of the porous tubing.

When the extent of either the stretching or the expansion is larger than the other, the length and the number of the small fibers are larger in the direction of the larger stretching or expansion but the length and number of the small fibers are smaller in the direction perpendicular to the above.

Electromicroscopic observation has now confirmed that the size of the nodes and the fibers of the porous tubing subjected to stretching and expansion in two directions are markedly different as compared to those of a porous tubing stretched or expanded in one direction only. In particular, it has also been confirmed that the direction of the fibers is more strongly distributed radially in the inner surface than the outer surface of the porous tubing.

The size of the nodes becomes smaller and smaller depending on the stretching ratio employed and the form of the nodes is a slender ellipsoid when a tube is stretched in one direction only. When a tube is stretched in two directions, the size of the nodes becomes about ⅓ to 1/10 of the size of the nodes of the porous tubing stretched in one direction only and at the same time the form of the nodes becomes almost spherical.

When the tube is stretched in one direction, the size of the fibers in the porous tubing is almost a constant value of about 0.5 to 1 micron regardless of the stretching ratio but when the tube is stretched in two directions, the size of the fibers can be reduced to about ⅓ to 1/5 of the above and the number of the fibers increased depending on the reduction in size.

Thus, the first embodiment of the porous tubing of this invention has very excellent flexibility and tear resistance and is a composite tubular article not known until now.

Each of the second embodiment and the third embodiment of the porous tubing of this invention also has excellent flexibility and, for example, when the porous tubing has an outer diameter of 6.0 mm and an inside diameter of 5.0 mm, the tubing will be completely deformed into a compressed body under a load of 10 g. The compressed material of the porous tubing has a sufficient sealing property to gases and liquids for use as a heat resisting and chemical resisting gasket or packing and is useful as a sealing material for large flanges.

A metallic packing made of copper or aluminum may have excellent heat resistance but in order to obtain a sealing capability, it is necessary to compress the packing at a load above a few kilograms and further when the packing is used several times, the sealing property of the packing is greatly deteriorated by the compression since a plastic flow occurs due to the compression.

A band-form sealing material composed of polytetrafluoroethylene is also used but such a sealing material has not been subjected to a heat treatment and the material is used only once for the purpose of sealing.

Each of the second embodiment and the third embodiment of the porous tubing of this invention has been subjected to a heat treatment at a temperature of at least about 327° C. at the outer surface of the tube and hence after using the porous tubing as a sealing material, the structure thereof was less changed and a complete sealing using a slight compressive force can be attained with the porous tubing.

The temperatures at stretching and expanding the tube are explained below in detail.

The size and form of a tube can be changed by stretching or expansion but in order to change the size and form of the tube, a force must be applied to the tube from at least the outside. As is generally the case with thermoplastic materials, the force required decreases as the temperature of the tube increases and the force required decreases as the temperature of the tube decreases. The force required for deforming the tube must be compared with the strength of the tube itself which is obtained in a fibrous oriented state by extrusion.

The strength of the tube achieved by extrusion depends greatly upon the conditions of the extrusion molding but does not depend to a great extent on the temperature and atmosphere after molding.

When the tube is stretched or expanded at a temperature below a particular temperature, the external force required for causing the deformation is larger than the strength of the tube and hence the tubes tend to be ruptured during deformation. On the other hand, when the tube is stretched or expanded at a temperature higher than a particular temperature, the external force required for causing the deformation is less than the strength of the tube and the tendency toward rupture of the tube is reduced suddenly. Thus, for carrying out the deformation of the tube, it is necessary to define the lower limit of the temperature depending on the conditions of extrusion molding.

The same tendency as above is present in the deformation rate of stretching and expansion. When the deformation rate increases, the external force required for causing the deformation of the tube increases and thus in order to not break the tube, it is necessary to heat the tube to a higher temperature.

Since the strength of the tube changes according to the conditions of extrusion molding, the minimum temperature in the deformation of the tube cannot be defined clearly but the temperature can be easily understood by persons skilled in the art.

The sintering step employed in this invention means a step of heating the stretched and stretched/expanded tube at a temperature higher than about 327° C. while fixing the tube to prevent its shrinkage.

The tube is, as a matter of course, fixed so that the tube does not shrink in the longitudinal direction. It is one of the important steps of this invention to sinter the tube while fixing the tube in the radial direction by evacuating the surrounding atmosphere. Vacuum fixing in the radial direction can be employed in a sintering furnace or directly after sintering but the tube fixed in the longitudinal direction is first heated to a temperature higher than about 327° C. and then must be fixed in the radial direction before the tube is cooled to a temperature below about 327° C.

The vacuum system surrounding the tube can be practiced if the following conditions are satisfied. That is, (1) when the tube is fixed in the radial direction by evacuating the surrounding atmosphere of the tube, the amount of air withdrawn by the vacuum pump is controlled so that it is as small as possible but the extent of evacuation is that capable of fixing the tube in in the radial direction, (2) the temperature of the tube is kept at a temperature higher than about 327° C. until the tube is fixed in the radial direction and after being so fixed, the tube is cooled to a temperature below about 327° C. and crystallized, and (3) a pipe determining the diameter of tube after expansion has suction holes or a slit but equipment sealing parts having a diameter smaller than the diameter of the expansion pipe must be satisfactory. Factor (1) indicated above is important in particular. That is, when the amount of air withdrawn is too large, the air in the inner cavity of the tube is withdrawn through the wall after the tube is fixed in the radial direction whereby the tube is ruptured due to evacuation at both sides of the pipe for vacuum fixing.

To assist in understanding this invention, the invention will be explained by referring to the accompanying drawings.

Figure 1:
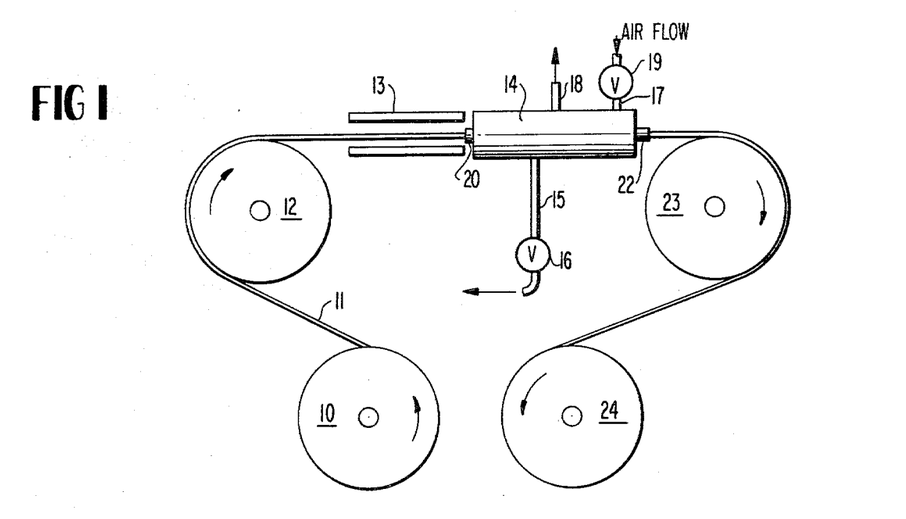
FIG. 1 is a schematic partial side view of an apparatus suitably used for practicing the process of this invention.

FIG. 1 is a schematic side view showing an apparatus for practicing the process of this invention.

A tube 11 wound around a supply bobbin 10 is unwound and passed through a heating furnace 13 at a constant speed by means of a driving capstan 12. Tube 11 from the heating furnace 13 in a condition heated to a temperature of higher than about 327° C. is introduced into a vacuum case 14 for fixing in the direction at such a high speed that the temperature of the tube 11 does not drop to a temperature below about 327° C. The reduced pressure in the vacuum case 14 is maintained at a definite value by means of a control valve 16 while evacuating the vacuum case through a pipe 15 connected to a vacuum pump (not shown). On the other hand, the vacuum case 14 is equipped with an air inlet pipe 17 and an outlet pipe 18 for passing air therethrough for cooling the tube below about 327° C. immediately after the tube is fixed in the radial direction and the cooling rate is controlled by opening or closing valve 19. The tube 11 is passed through the vacuum case 14 as described above. For maintaining the vacuum case 14 at a definite reduced pressure, a sealing die 20 and a sealing die 22 are positioned at the inlet side and the outlet side of the vacuum case, respectively.

The tube 11 fixed in the radial direction and cooled below about 327° C. and crystallized is coiled around a reel 24 through a driving capstan 23. In heating the tube 11 to a temperature higher than about 327° C. a convey force is applied from a same driving motor (not shown) to the driving capstan 12 and the driving capstan 23 to rotate both capstans at the same rotary speed, whereby the tube is fixed in the longitudinal direction to prevent shrinkage and the tube is also fixed in the radial direction thereof due to the evacuation force in the vacuum case 14 to prevent radial shrinkage.

Figure 2:
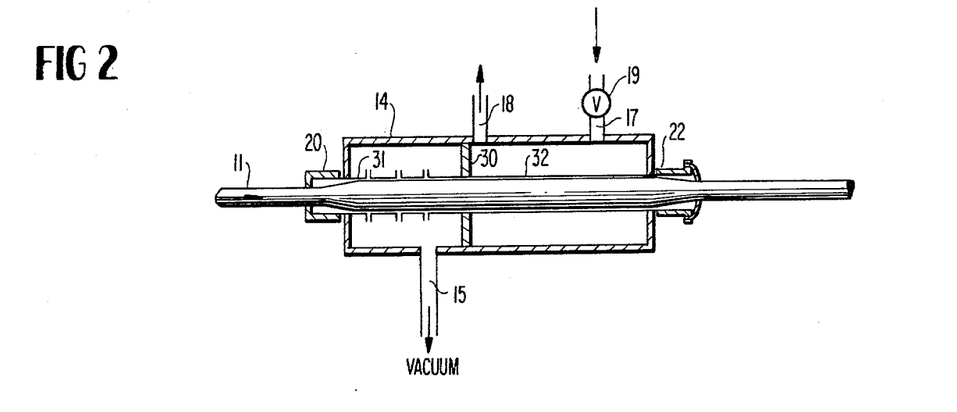
FIG. 2 is an enlarged sectional view of the vacuum case used in the apparatus shown in FIG. 1.

FIG. 2 is an enlarged sectional view showing the vacuum case 14 used in this invention. Tube 11 heated to a temperature above about 327° C. passes through a sealing die 20 and in this case, in order to complete the sealing, the opening of the sealing die is so formed that the diameter of the opening coincides with the outer diameter of the tube 11 having the increased volume as the result of being heated to a temperature above about 327° C. In order to reduce the friction reducing the driving speed of the driving capstans 12 and 23 as low as possible, the thickness of the sealing part having the minimum hole must be less than 3 mm, preferably about 1 mm. The tube passed through the sealing hole enters a radial fixing pipe 31 evacuated through fine holes equipped to pipe 31, whereby the tube begins to expand in the radial direction and the outer surface of the tube comes into contact closely with the inner wall of the radial fixing pipe 31. The inside surface of the radial fixing pipe 31 must be smooth to an extent such that the tube is not too closely brought into contact with the inside surface of the pipe 31 to prevent a stretching of the tube by the driving capstans 12 and 23. In the vacuum case 14, an expansion section of tube 11 by evacuation is connected to a cooling section for crystallization after expansion through a heat insulating partition wall 30.

Since the tube 11 shrinks in the radial direction to some extent by being cooled to a temperature below about 327° C. in a cooling pipe 32, a space is formed between the cooling pipe and the tube 11. The formation of such a space is preferred for reducing the friction. Finally the tube 11 reaches an outlet sealing die 22.

Figure 3:
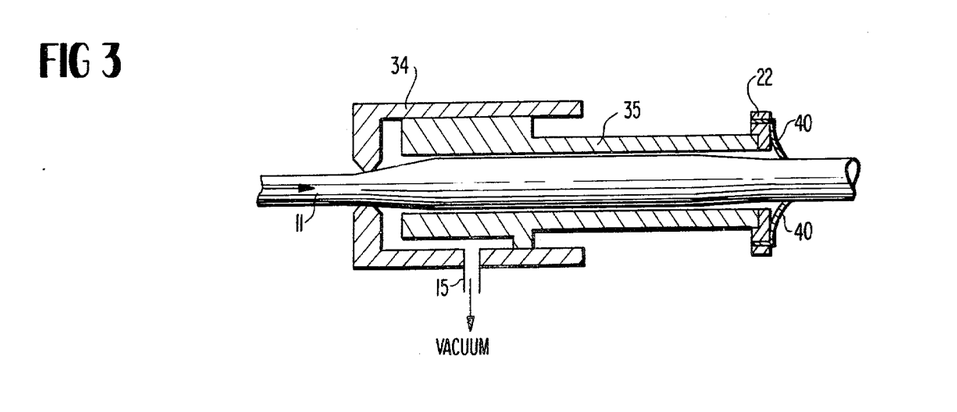
FIG. 3 is an enlarged sectional view of another vacuum case used in the apparatus for producing the porous tubing of this invention.

FIG. 3 is a cross sectional view showing the inside structure of the slit type vacuum case 14. The tube 11 enters the vacuum chamber through a sealing die equipped to the inlet portion of an outer frame 34, whereby the tube 11 is expanded and comes into close contact with the inside surface of the radial fixing pipe 35. In the embodiment shown in this figure, the radial fixing pipe 35 is cooled by the surrounding air. The outer frame 34 and the radial fixing pipe 35 of the vacuum case 14 are slidable with each other in order to change the room of the vacuum chamber, whereby the room of the vacuum chamber can be brought to optimum conditions capable of expanding the tube most preferably.

A rubber diaphragm 40 is equipped to sealing die 22 at the outlet side of the vacuum case to prevent leakage of air from the interlayer between the sealing die 22 and the tube 11. The room of the vacuum chamber determined by the outer frame 34 and the radial fixing pipe 35 must be adjusted or changed according to the diameter, wall thickness, travelling speed and the temperature of the tube 11. In order that the air in the inner cavity of the tube 11 is not withdrawn through the wall of the tube, it is preferred for the room of the vacuum chamber to be as small as possible. It has been confirmed that the interval of the space between the outer frame 34 and the fixing pipe 35 be preferably less than 3 mm, more preferably about 1 mm.

In this case, by heating the tube externally while cooling the inner surface of the tube by passing air through the inner cavity of the tube, the porous fibrous structure of the tubing can be changed between the inner surface of the tubing and the outer surface of the tubing. Also, by increasing the amount of the air passing through the inner cavity of the tube or lowering the temperature of the air passing through the inner cavity of the tube, it is possible to heat the outer surface of the tube to a temperature higher than about 327° C. and to heat the inner surface of the tube to a temperature lower than about 327° C. The outer surface only of such a tubing is sintered but the inner surface of the tubing is in an unsintered state and hence the form and the size of the fibers and the nodes differ between the inner surface and the outer surface of the tubing.

Furthermore, by reducing the amount of air passing through the inner cavity of the tube or increasing the temperature of the air passing through the inner cavity (practically speaking, by increasing the length of the heating furnace or increasing the temperature of the heating furnace), the inner portion of the tube can be heated to a temperature higher than about 327° C. but in this case the fibers of the polytetrafluoroethylene are exposed to a temperature higher than about 327° C. for a longer period of time and thus the fiber structure (in particular, the size of the fibers) of the outer surface portion of the tubing which was almost the same as that at the inner surface portion of the tubing, increases in size by causing a combination or fusion of two of more fibers. Also, by changing the amount of cooling air passing through the inner cavity of the tube and the amount of heat supplied externally, the thickness of the inner surface fibrous structure portion of the tubing can be changed from the outer surface fibrous structure portion of the tubing. The size of the fibers and the form of the nodes change greatly according to the temperature of the tube as described before.

Figure 4:
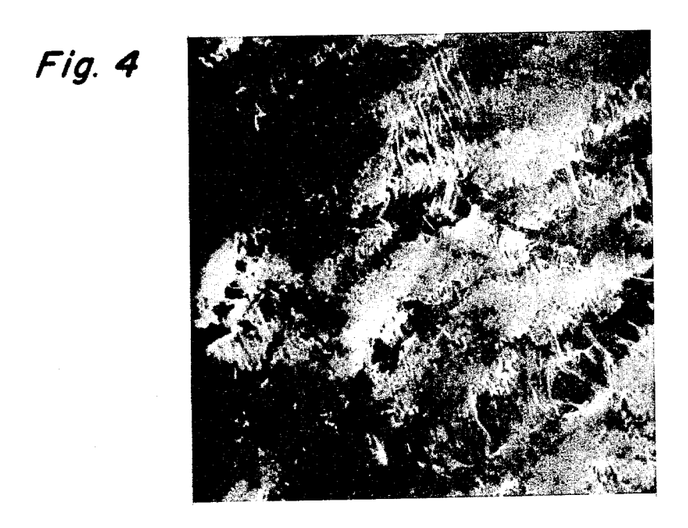
FIGS. 4–8 are scanning electron microphotographs of the porous polytetrafluoroethylene resin tubings of this invention.

FIG. 4 of the accompanying drawings is an electromicroscopic photograph of a porous polytetrafluoroethylene tubing in a state where the stretched or expanded tube is heated at a temperature lower than about 327° C. As is shown in the photograph, a large number of small cracks 1 exist throughout the entire surface of the wall of the tube. In the cracks 1, a large number of fibers 2 are aligned in parallel to the direction of stretching or expansion. The electromicroscopic photographs in FIG. 4 and in the subsequent figures have a degree of magnification of 400.

Nodes 3 which were subjected to the heat treatment at a temperature not higher than about 327° C. have a complicated form which is partitioned by the cracks 1 at the interface and has a large number of projections.

Figure 5:
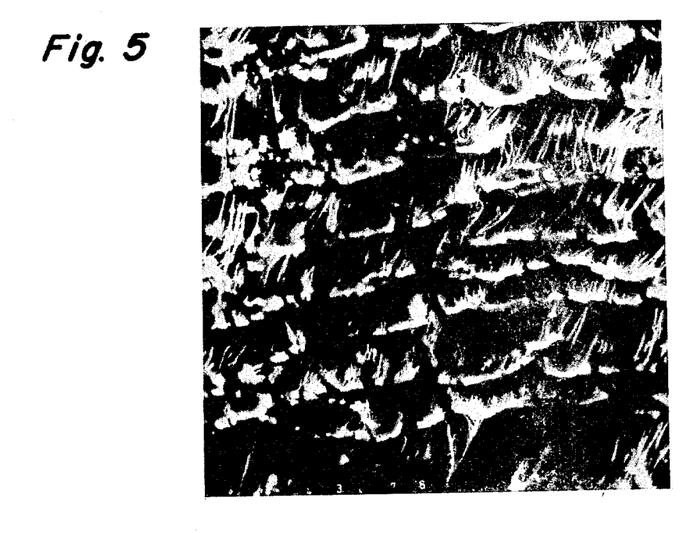

FIG. 5 is also an electromicroscopic photograph showing a porous tetrafluoroethylene tubing in the state where the stretched or expanded tube is heated to a temperature higher than about 327° C. but the polytetrafluoroethylene is incompletely sintered. In this state, the nodes 3, which have a complicated form at a temperature lower than 327° C., are melted and become round to some extent but the nodes 3 are not yet welded to the fibers 2 and are simply pressed thereagainst. However, it will be understood that the length of the fibers 2 in FIG. 5 is far longer than that of the fibers in FIG. 4.

Thus, the state of "the formation of crack 1" in FIG. 4 changed into the state that "fibers 2 and the nodes 3 are connected together" in FIG. 5.

Figure 6:
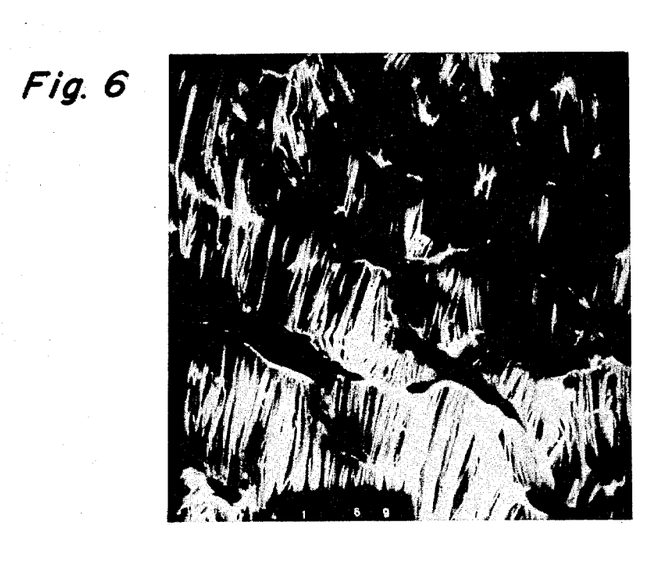

FIG. 6 is an electromicroscopic photograph of porous polytetrafluoroethylene tubing in the state where the nodes 3 are completely melted and thus are welded to the fibers 2, and also the fibers are regularly aligned in the stretched or expanded direction.

The size of the fibers in FIG. 5 is almost the same as that in FIG. 6 but the form of the nodes differs considerably between the tubes in FIG. 5 and FIG. 6.

Figure 7:
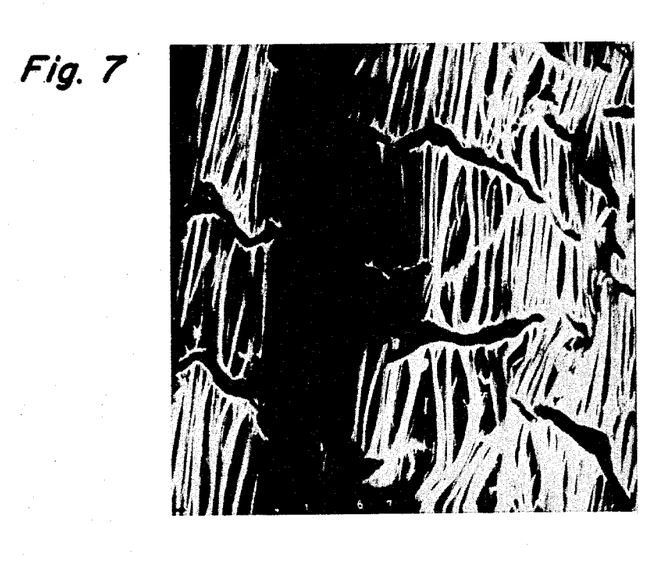

FIG. 7 is also an electromicroscopic photograph of a porous polytetrafluoroethylene tubing in the state where the tube was subjected to the heat treatment at a temperature higher than about 327° C. for a long period of time. The form of the nodes is almost the same as that of the nodes in FIG. 6 but the size of the fibers 2 is bigger than that of the fibers in FIG. 6 and the number of the fibers 2 is less than that in FIG. 6.

The tubular porous articles of this invention include the composite fibrous structures having an outer surface structure and an inner surface structure as illustrated in FIG. 5 and FIG. 4, FIG. 6 and FIG. 5, and FIG. 7 and FIG. 6 respectively.

Figure 8:
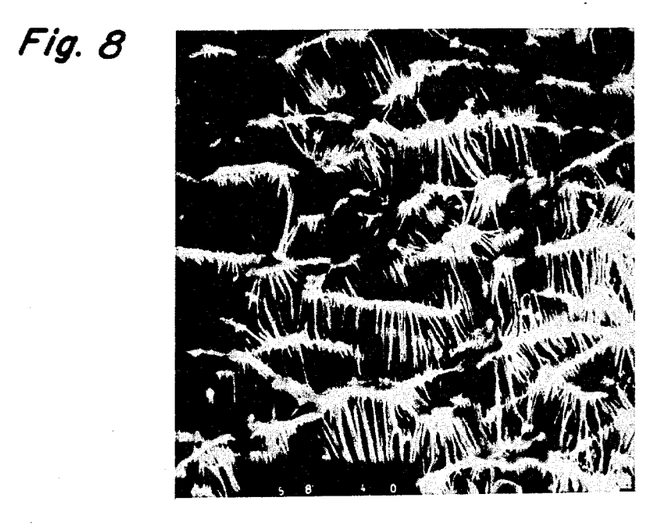

FIG. 8 is also an electromicroscopic photograph of a porous polytetrafluoroethylene tubing in the state where the tube was subjected to the same heat treatment as in FIG. 6 but in this case, since the tube was subjected to both stretching and expansion, the direction of the fibers 2 among the nodes 3 is distributed radially centering the nodes 3.

The following examples are given to illustrate the invention in greater detail. Unless otherwise indicated, all parts, percentages, ratios and the like are by weight.

EXAMPLE 1

3 kg of fine powders of F-103 (trade name for a polytetrafluoroethylene produced by Daikin Kogyo Co., Ltd. was mixed with 0.86 Kg of V.M. & R naphtha (density: 0.752, viscosity: 2.4 C.P., boiling point range: 120°–145° C.; produced by Shell Oil Co.). The resulting mixture was molded at a pressure of 10 Kg/cm$^2$ into a cylindrical form, and then was charged to a ram extruder (inner diameter of the cylinder: 60 mm, outer diameter of mandrel: 10 mm). Extrusion was carried out using a die capable of molding a tube having an outer diameter of 5.0 mm and an inner diameter of 4.0 mm at a linear tube speed of 1 m/min. at a pressure of 300 kg/cm$^2$.

After the tube thus-produced was rolled up on a bobbin, it was immersed in trichloroethylene to remove the VM & R naphtha oil component completely. The thus treated tube was stretched to a length of 3 times the original length by passing it between a supply capstan (speed of 25 m/min) and a take up capstan (speed of 75 cm/min) with a furnace kept at 380° C. being provided between the two capstans. The thus streched tube become slightly thinner and had an outer diameter of 4.8 mm and an inner diameter of 3.9 mm. The stretching could be done continuously and uniformly.

The strecthed tube was sintered and expanded using a vacuum case as shown in FIG. 2. The temperature of the furnace was 440° C. at the inlet thereof, 490° C. at the center thereof and 400° C. at the outlet thereof. An inlet sealing die had an opening of a diameter of 5.0 mm and a die length of 1 mm. The die was kept at 385° C. The inner diameters of a radial fixing pipe was 5.2 mm and a silicone rubber packing at the outlet side was had a hole of 5.0 mm in diameter. Tube was passed through the vacuum case of which the degree of reduced pressure was controlled using a control valve to −65 cmHg and sintered and expanded to form a tubing having an outer diameter of 5.0 mm and an inner diameter of 4.3 mm.

The thus obtained tubing had a porosity of 78% and a suture tear resistance of 450 g/mm. Different bubble point values depending on the method of measurement were obtained. The bubble point was determined by immersing the tubing in isopropyl alcohol, introducing air into the tubing from one surface (outer or inner) thereof and measuring the pressure at which bubbles appeared for the first time (hereinafter "bubble point").

When air was introduced into the inner cavity of the tubing the bubble point was 0.28 Kg/cm$^2$ while when it was introduced from the exterior of the tubing the bubble point was 0.19 Kg/cm$^2$.

The above difference in bubble point depending upon the manner of measurement is ascribable to the fact that the pore size on the inner surface of the tubing is smaller than that on the outer surface thereof. FIG. 6 is an electromicroscopic photograph of the inner surface of the tubing and FIG. 7 is an electromicroscopic photograph of the outer surface of the tubing.

EXAMPLE 2

A tubing was prepared in the same manner as in Example 1 except that the tube was sintered and expanded at a linear speed of 130 cm/min. The thus obtained tubing had an outer diameter of 5.2 mm, an inner diameter of 4.4 mm, a porosity of 81% and a suture tear strength of 180 g/mm. Further, the bubble point of the tubing from the inner surface was 0.31 Kg/cm$^3$ and the bubble point from the exterior surface was 0.28 Kg/cm$^2$. The appearance of the outer surface coincided with that as shown in FIG. 6 and the appearance of the inner surface coincided with that shown in FIG. 5.

COMPARATIVE EXAMPLE 1

A tubing was prepared in the same manner as in Example 1 except that the reduced pressure control valve of the vacuum case was closed completely. The thus obtained tubing had an outer diameter of 4.6 mm, an inner diameter of 3.7 mm, a porosity of 68% and a suture tear strength of 300 g/mm. The inner surface and exterior surface bubble points coincided and were 0.28±0.03 Kg/cm$^2$ respectively. The texture of the inner surface and outer surface of the tubing the inner surface and outer surface resembled that shown in FIG. 6.

EXAMPLE 3

A tubing was prepared in the same manner as in Example 1 except that the inner diameter of the radial fixing pipe in the vacuum case was 8 mm. The thus obtained tubing had an outer diameter of 7.8 mm, an inner diameter of 7.1 mm, a porosity of 83%, a suture tear strength of 420 g/mm. The bubble point from the inner surface was 0.38 Kg/cm$^2$ and the bubble point from the outer surface was 0.29 Kg/cm$^2$. The appearance of the inner surface coincided with that shown in FIG. 8.

EXAMPLE 4

A tubing was prepared in the same manner as in Example 1 except that the inner diameter of the radial fixing pipe in the vacuum case was 12 mm and the value of reduced pressure in the vacuum case was −70 cmHg. The thus obtained tubing had a porosity of 91%, a bubble point from the inner surface of 0.29 Kg/cm and a bubble point from the outer surface of 0.12 Kg/cm$^2$.

EXAMPLE 5

A tubing was prepared in the same manner as in Example 2 except that the temperature of the heating furnace was 480° C. at the inlet thereof, 520° C. at the center thereof and 420° C. at the outlet thereof and that the temperature of the vacuum case was 400° C. The thus obtained tubing had an outer diameter of 5.2 mm, an inner diameter of 4.5 mm, a porosity of 79% and a suture tear strength of 630 g/mm. The bubble point from the inner surface was 0.27 Kg/cm$^2$ and the bubble point from the outer surface was 0.17 Kg/cm$^2$.

EXAMPLE 6

A tubing was prepared in the same manner as in Example 1 except that the stretching of the tube was carried out at a supply capstan speed of 50 cm/min and a take up capstan speed of 300 cm/min to a length of 6 times the original length, the temperature of the heating furnace was 400° C. at the inlet thereof, 460° C. at the center thereof and 380° C. at the outlet thereof and the temperature of the vacuum case was 365° C. The thus obtained tubing had a different inner surface bubble point from that of the outer surface.

While the invention has been described in detail and with reference to specific embodiments thereof, it will be apparent to one skilled in the art that various changes and modifications can be made therein without departing from the spirit and scope thereof.

What is claimed is:

1. A process of producing a porous polytetrafluoroethylene tubing which comprises forming a tubing of a mixture of an unsintered polytetrafluoroethylene containing a liquid lubricant, stretching the tube at least in the longitudinal direction, and heating the tube in a stretched state in such a manner that the outer surface of the tube is heated at a temperature higher than about 365° C. and the inner surface of the tube is heated at a temperature lower than the temperature of the outer surface of the tube, and wherein the temperature difference between the center of the heating furnace and the outer surface of the tube is at least 95° C.

2. The process as claimed in claim 1, wherein the tube is heated in a state stretched in at least the longitudinal direction of the tube in a manner such that the outer surface of the tube is heated at a temperature higher than about 365° C. while, in this case, reducing the pressure of the atmosphere surrounding said tube.

3. The process as claimed in claim 1, wherein the outer surface of the tube is heated to a temperature higher than about 365° C. while supplying cooling air through the inner cavity of the tube.

4. The process as claimed in claim 1, wherein between said forming and said stretching said liquid lubricant is removed from the tubing.

5. The process of claim 1, further comprising, after said stretching of the tube in at least the longitudinal direction, a subsequent expansion of the tube in the radial direction of the tube.

6. The process as claimed in claim 1, wherein said heating of said tube in said stretched state is conducted while preventing shrinkage of said tube in the longitudinal direction.

7. The process as claimed in claim 6, wherein following said heating of the tube, the tube is fixed in the radial direction before the tube is cooled to a temperature below about 365° C.

8. A process of producing a porous polytetrafluoroethylene tubing which comprises forming a tubing of a mixture of an unsintered polytetrafluoroethylene containing a liquid lubricant, stretching the tube at least in the longitudinal direction, and heating the tube in a stretched state in such a manner that only the outer surface of the tube is sintered and the inner surface of the tube remains unsintered.

9. The process as claimed in claim 8, wherein the tube is heated in a state stretched in at least the longitudinal direction of the tube in a manner such that the outer surface of the tube is sintered and the inner surface of the tube remains unsintered while, in this case, reducing the pressure of the atmosphere surrounding said tube.

10. The process as claimed in claim 8, wherein the outer surface of the tube is sintered and the inner surface of the tube remains unsintered while supplying cooling air through the inner cavity of the tube.

11. A process of producing a porous polytetrafluoroethylene tubing which comprises forming a tubing of a mixture of an unsintered polytetrafluoroethylene containing a liquid lubricant, stretching the tube at least in the longitudinal direction, and heating the tube in a stretched state in such a manner that the outer surface of the tube is heated at a temperature higher than about 327° C. and the inner surface of the tube is heated at a temperature lower than the temperature of the outer surface of the tube, said heating being carried out in a manner such that only the outer surface of the tube is sintered and the inner surface of the tube remains unsintered.

* * * * *